United States Patent
Siby Kurian et al.

(10) Patent No.: US 11,915,089 B2
(45) Date of Patent: Feb. 27, 2024

(54) FARADAY CAGE FOR DIGITAL SET SCREW PROBE READER

(71) Applicant: Warsaw Orthopedic, Inc., Warsaw, IN (US)

(72) Inventors: Arjun Siby Kurian, Memphis, TN (US); Kevin T. Foley, Germantown, TN (US); Newton H. Metcalf, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 42 days.

(21) Appl. No.: 17/371,160

(22) Filed: Jul. 9, 2021

(65) Prior Publication Data

US 2023/0009063 A1 Jan. 12, 2023

(51) Int. Cl.
*G06K 7/10* (2006.01)
*A61B 17/70* (2006.01)
*A61B 17/68* (2006.01)

(52) U.S. Cl.
CPC ........ *G06K 7/10366* (2013.01); *A61B 17/685* (2013.01); *A61B 17/7032* (2013.01); *G06K 7/10297* (2013.01)

(58) Field of Classification Search
CPC .................................................. G06K 7/10366
See application file for complete search history.

(56) References Cited

U.S. PATENT DOCUMENTS

| | | |
|---|---|---|
| 4,781,591 A | 11/1988 | Allen |
| 5,383,935 A | 1/1995 | Shirkhanzadeh |
| 6,004,349 A | 12/1999 | Jackson |
| 6,026,331 A * | 2/2000 | Feldberg ................ A61B 18/18 607/102 |
| 6,120,502 A | 9/2000 | Michelson |
| 6,280,445 B1 | 8/2001 | Morrison et al. |
| 6,292,699 B1 | 9/2001 | Simon et al. |
| 6,485,491 B1 | 11/2002 | Farris et al. |
| 7,455,672 B2 | 11/2008 | Michelson |
| 8,057,519 B2 | 11/2011 | Justis et al. |
| 8,147,549 B2 | 4/2012 | Metcalf, Jr. et al. |
| 8,494,644 B2 | 7/2013 | Cowan et al. |
| 8,838,249 B2 | 9/2014 | Nycz |
| 8,868,200 B2 | 10/2014 | Abrahamson et al. |
| 9,241,738 B2 | 1/2016 | Quevedo et al. |
| 9,498,294 B2 | 11/2016 | Rigsby et al. |
| 2005/0267477 A1 | 12/2005 | Jackson |

(Continued)

*Primary Examiner* — Rafferty D Kelly

(74) *Attorney, Agent, or Firm* — FOX ROTHSCHILD LLP

(57) ABSTRACT

A medical implant identification system is disclosed. The implant identification system may include a probe reader extending from a proximal end to a distal end and the distal end may include a faraday cage. The probe reader may be in communication with an operating room computer and/or a display. The implant identification system may include at least one digital set screw comprising an antenna disposed in an antenna portion of the digital set screw. In various embodiments, the faraday cage may have a size and shape corresponding to a size and shape of the antenna portion of the digital set screw. Additionally, the antenna may be configured to transmit identity information to the probe reader, and the identify information may be displayed by the display and/or stored in a data store of the operating room computer.

20 Claims, 10 Drawing Sheets

(56) References Cited

U.S. PATENT DOCUMENTS

| | | |
|---|---|---|
| 2009/0234391 A1 | 9/2009 | Butler et al. |
| 2010/0201118 A1 | 8/2010 | Anton et al. |
| 2010/0298886 A1 | 11/2010 | Kraus et al. |
| 2011/0118852 A1 | 5/2011 | Evans |
| 2014/0114382 A1 | 4/2014 | Kim |
| 2014/0212471 A1 | 7/2014 | Drapeau et al. |
| 2015/0190242 A1 | 7/2015 | Blain et al. |
| 2016/0270927 A1 | 9/2016 | Zellmer et al. |
| 2017/0007420 A1 | 1/2017 | Stevenson et al. |
| 2019/0298478 A1* | 10/2019 | Aquino ............... A61B 17/3421 |
| 2020/0022733 A1 | 1/2020 | Benson et al. |
| 2020/0022735 A1 | 1/2020 | Fields et al. |
| 2020/0022739 A1 | 1/2020 | Benson et al. |
| 2020/0022740 A1 | 1/2020 | Benson et al. |
| 2020/0022772 A1 | 1/2020 | Benson et al. |

\* cited by examiner

FARADAY CAGE FOR DIGITAL SET SCREW PROBE READER

CROSS-REFERENCE TO RELATED APPLICATIONS

This Application incorporates by reference U.S. Nonprovisional patent application Ser. No. U.S. 16/039,592 entitled "Load sensing assembly for a spinal implant," filed Jul. 19, 2018; U.S. Nonprovisional patent application Ser. No. U.S. 16/395,212 entitled "Break Off Set Screw with Offset Hex," filed Apr. 25, 2019; U.S. Nonprovisional patent application Ser. No. U.S. 16/395,216 entitled "Set Screw Sensor Placement," filed Apr. 25, 2019; U.S. Nonprovisional patent application Ser. No. U.S. 16/395,221 entitled "Antenna Placement for a Digital Set Screw," filed Jul. 3, 2019; and U.S. Nonprovisional patent application Ser. No. U.S. 16/509,285 entitled "Temp Sensing Array for Set Screw Infection Monitoring," filed Jul. 11, 2019. The disclosures of each patent application listed above is fully incorporated into this document by reference in their entirety.

FIELD

In one aspect, the present technology is generally related to mechanical and electrical sensor digital set screw assemblies for implant devices and systems that are readable by a probe.

BACKGROUND

Conventional set screws lack a means to verify fusion status, load status, and/or hardware failure. A need exists to be able to verify and assign location information of set screws used in a medical context.

SUMMARY

Intra-operative reading of information, or labeling, of an implant such as, for example, a set screw, can be technologically challenging due to the close proximity of multiple digital set screws because the antennas of each digital set screw can create cross talk and/or interference between the set screws which can lead to potentially mislabeling of the various set screws. Correct labeling of set screws within the spinal implant system and/or spinal construct is essential for set screw specific postoperative monitoring, e.g., fusion status, load status, and/or hardware failure. A need exists for a way to block the interference or cross talk of a plurality of set screws of a spinal construct when labelling a specific set screw.

The techniques of this disclosure generally relate to a probe reader including a faraday cage for reading and/or assigning identity information such as location information of a first set screw of a plurality of set screws.

In one aspect, the present technology is related to a probe reader having a faraday cage for individually reading information from a single set screw of a plurality of set screws of an implant system. In another aspect, the present technology is related to a method for labelling and/or reading information from a digital set screw of a plurality of digital set screws of an implant system while blocking interference from the other set digital set screws.

In one aspect, the present disclosure provides a medical implant identification system, for example. The system may include a probe reader extending from a proximal end to a distal end in a proximal-to-distal direction, and the distal end may include a faraday cage and/or a faraday cage, for example. In various embodiments, a display and/or an operating room computer may be in communication with the probe reader, for example. In various embodiments, the system may include a set screw comprising an antenna disposed in an antenna portion of the set screw and at least one sensor in communication with the antenna, for example. In various embodiments, the faraday cage may have a size and shape corresponding to a size and shape of the antenna portion, for example. In various embodiments, the antenna may be configured to transmit identity information to the probe reader, for example. Additionally, the antenna may be configured to transmit sensor information received from the at least one sensor to an external device, for example.

In another aspect, the disclosure provides a medical implant identification system, for example. The system may include a probe reader extending from a proximal end to a distal end in a proximal-to-distal direction, and the distal end may include a faraday cage, for example. In various embodiments, the system may include a display in communication with the probe reader and/or an operating room computer, for example. In various embodiments, the system may include a first set screw comprising an antenna disposed in a first antenna portion of the first set screw and at least one first sensor in communication with the first antenna, for example. Additionally, in various embodiments, the system may include a second set screw having a second antenna disposed in a second antenna portion of the second set screw and at least one second sensor in communication with the first antenna, for example. In at least some embodiments, the faraday cage may have a size and shape corresponding to a size and shape of the first antenna portion and the second antenna portion, for example. In various embodiments, the first antenna may be configured to transmit first identity information to the probe reader, and may be configured to transmit first sensor information received from the at least one sensor to an external device, for example. Additionally, in various embodiments, the second antenna may be configured to transmit second identity information to the probe reader, and may be configured to transmit second sensor information received from the at least one second sensor to an external device, for example.

In another aspect, a method for isolating identity information of a set screw, is provided. The method may include the step of providing a medical implant identification system, for example. In various embodiments, the medical implant identification system may include a probe reader extending from a proximal end to a distal end in a proximal-to-distal direction, and the distal end may include a faraday cage, for example. In various embodiments, a display may be in communication with the probe reader, for example. In various embodiments, an operating console may be in communication with the probe reader, for example. In various embodiments, a first set screw comprising an antenna disposed in a first antenna portion of the first set screw and at least one first sensor in communication with the first antenna may be provided. Additionally, in various embodiments, a second set screw comprising a second antenna disposed in a second antenna portion of the second set screw and at least one second sensor in communication with the first antenna, may be provided. Additionally, in at least some embodiments, the faraday cage may have a size and shape corresponding to a size and shape of the first antenna portion and the second antenna portion, for example. In various embodiments, the first antenna may be configured to transmit first identity information to the probe reader, and may be configured to transmit first sensor information received from the at least one sensor to an external device, for example. Additionally, in various embodiments, the second antenna may be configured to transmit second identity information to the probe reader, and may be configured to transmit second sensor information received from the at least one second sensor to an external device, for example. The method may further include the steps of positioning the faraday cage of the probe reader around the first antenna portion, receiving the first identity information of the first set screw, and blocking interference associated with the second identity information of the second set screw, for example. The method may also include the steps of positioning the faraday cage of the probe reader around the second antenna portion, receiving the second identity information of the second set screw, and blocking interference associated with the first identity information of the first set screw, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
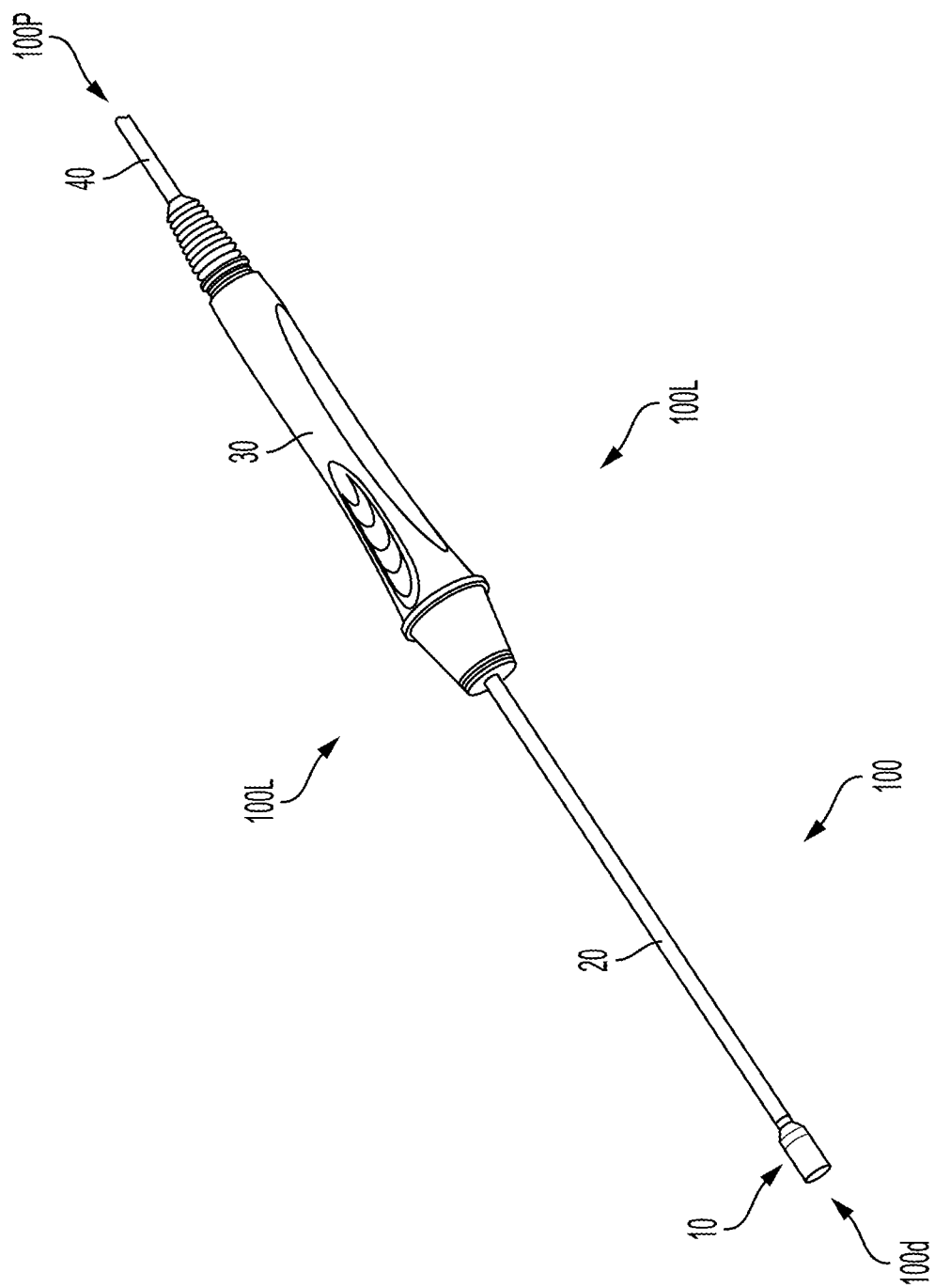
FIG. 1 is a perspective view of a surgical probe reader.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 2:
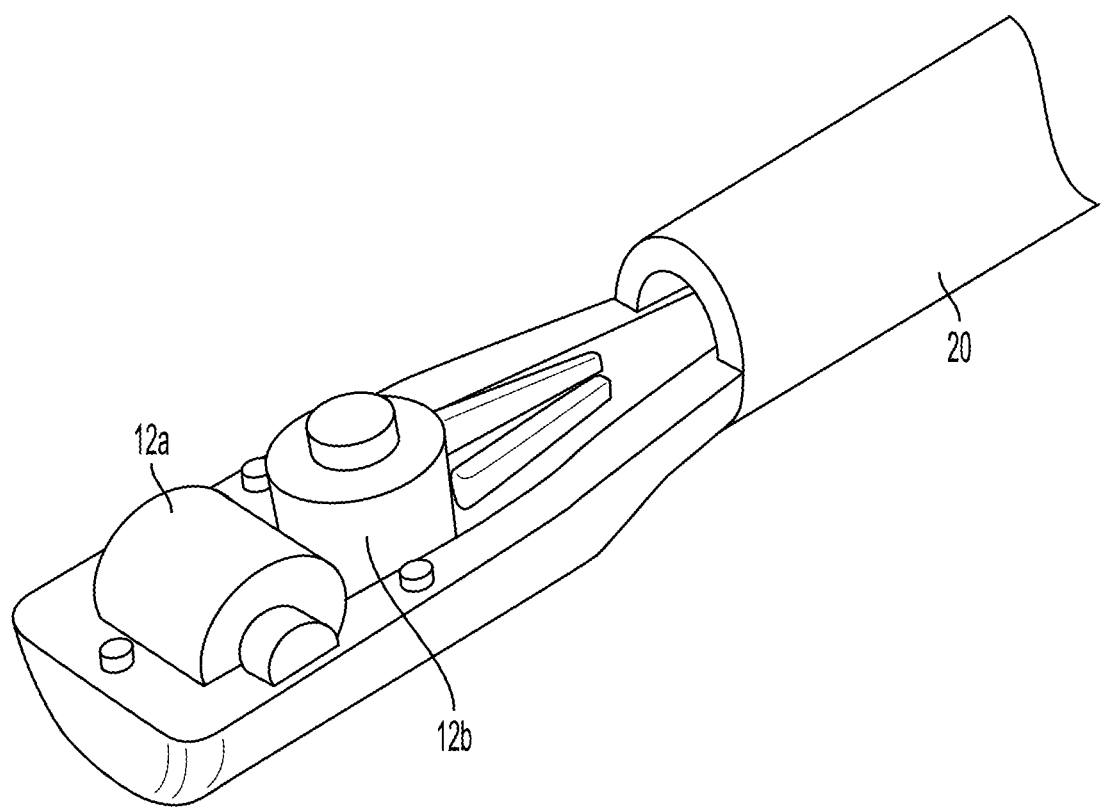
FIG. 2 is a perspective view of a distal end of a surgical probe reader.

Referring to FIGS. 1-9 generally, various probe reader 100 embodiments, set screw 50 embodiments, and vertebral pedicle screw system 200 embodiments are disclosed. FIG. 1 is a perspective view of a surgical probe reader 100 and FIG. 2 is a perspective view of a distal end 100d of a surgical probe reader. In various embodiments surgical probe reader 100 may extend in a longitudinal direction from a proximal end 100p to a distal end 100d. Surgical probe reader 100 may have a width that extends in a lateral direction (or widthwise direction) between a first lateral side 1001 and a second lateral side 1001, for example. Surgical probe reader 100 may include a handle portion 30 having various ergonomic geometry for an under user to hold probe reader 100, for example. In various embodiments, handle portion 30 may be coupled to a shaft portion 20. In some embodiments, shaft portion 20 may be a rigid shaft and in other embodiments, (not illustrated) shaft portion may be formed of a flexible and or semi-rigid material. Handle portion 30 may include a through hole of which a connecting wire 40 passes through which may also extend through shaft portion 20, for example. A distal end 100d of probe reader 100 may include a faraday cage 10 (may also be referred to as a faraday shroud) securely connected to shaft portion 20, for example. Faraday cage 10 may be understood as having its ordinary technical meaning as would be understood by a person of skill in the art, e.g., a grounded metal screen surrounding a piece of equipment to exclude electrostatic and electromagnetic influences. As will be explained in more detail below, the faraday cage 10 may be configured to surround a first digital set screw 50 such that information and/or various signals may be received by the digital probe reader from the first digital set screw 50 while preventing, excluding, and/or suppressing interference from other electronic sources. For example, electromagnetic signals may be received from the first digital set screw 50 while other electromagnetic signals from other sources may be excluded and/or suppressed. In various embodiments, faraday cage 10 may be formed of a metallic material in the form of a hollow conductor whereby electromagnetic charge emanating from outside of the faraday cage 10 remains on the external surface of the faraday cage 10 and/or is reflected. Additionally, electromagnetic charge emanating from within the perimeter of faraday cage 10 may be read by probe reader 100.

FIG. 2 may illustrate portion of a distal end 100d of a probe reader 100 with some parts removed for ease of understanding. In various embodiments, the distal end 100d may comprise a first coil 12a and a second coil 12b. In various embodiments, the first coil 12a may extend in a first direction and the second coil 12b may extend in a second direction that is perpendicular to and/or orthogonal to the first direction. For example, the first coil 12a may extend in a first lateral direction (left to right with respect to probe reader) and the second coil 12b may extend in a second lateral direction (top to bottom and/or vertically) and be positioned such that a longitudinal axis of each coil 12a, 12b extends in a perpendicular direction. Those with skill in the art will recognize that other extension directions are also viable, although in some embodiments and environments it may be important to have each coil 12a, 12b extend in a direction orthogonal to and/or perpendicular to the other coil to maximize the ability to couple to various digital set screws 50 at various orientations. In some embodiments, the probe reader 100 may only take measurements within a relatively short range of about 0 mm to about 6 mm, and in other embodiments within a range of about 0 mm to about 3 mm. Those with skill in the art will appreciate that the probe reader 100 may energize a digital set screw 50 via inductive coupling, for example. Additionally, in various embodiments, the probe reader may be configured to read signals at a frequency of about 5 hz to about 10 hz, for example and various digital set screws 50 disclosed herein may be configured to transmit information at a frequency within a range of about 5 hz to about 10 hz, for example. Furthermore, in various embodiments the faraday cage 10 may cover the coils 12a, 12b and extend a distance from the distal end of probe reader 100.

Figure 3:
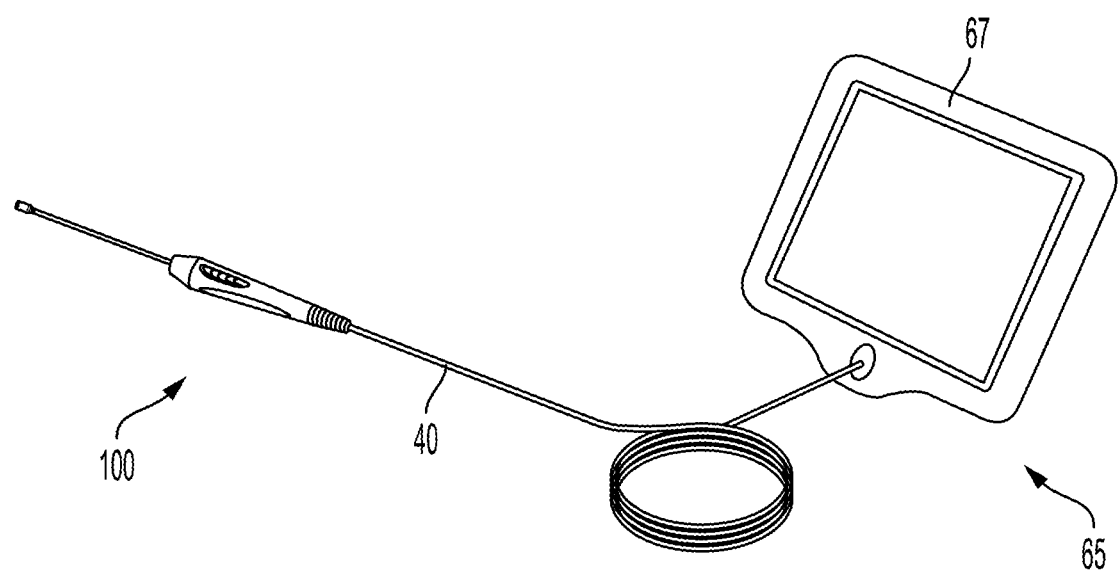
FIG. 3 is a perspective view of a surgical probe reader in communication with an external display and signal processing apparatus.

FIG. 3 is a perspective view of a surgical probe reader 100 in communication with an external display 67 and operating room console 65. In various embodiments, operating room console 65 may also be referred to as a signal processing apparatus, for example. In the example embodiment, the operating room console 65 may include a display 67 that may integral to the operating room console 65 or embodied as a separate display 67 distinct from the electronic components of operating room console 65. In the example embodiment, probe reader 100 may be in communication with operating room console 65 via communication wire 40. For example, a cable and/or fiber configured to transmit various signals received by probe reader 100. In various embodiments, probe reader 100 may receive power from operating room console 65 via communication wire 40. In practice, an end user such as a surgeon or technician may place probe reader 100 adjacent to and/or above a digital set screw 50 thereby charging the digital set screw. The probe reader 100 may receive identity information such as a tag or marker that is unique to the digital set screw and this unique identifying information may be transmit to the operating room console 65 and displayed on the display 67, for example. Thereafter, the end user may assign a specific name and/or installation location to the digital set screw on the basis of the unique identifying information. In other embodiments, the digital set screw 50 may not initially contain unique identifying information, but may still contain other information which can be used to assign a unique identifier to the digital set screw 50. For example, an end user such as a surgeon may assign unique identifying information and/or location information to a digital set screw 50 after it has been installed. In various embodiments, operating room console 65 may be configured to store the identifying information of the digital set screw 50 in a data set such as a table, spreadsheet, API interface, or similar, for example.

Figure 4:
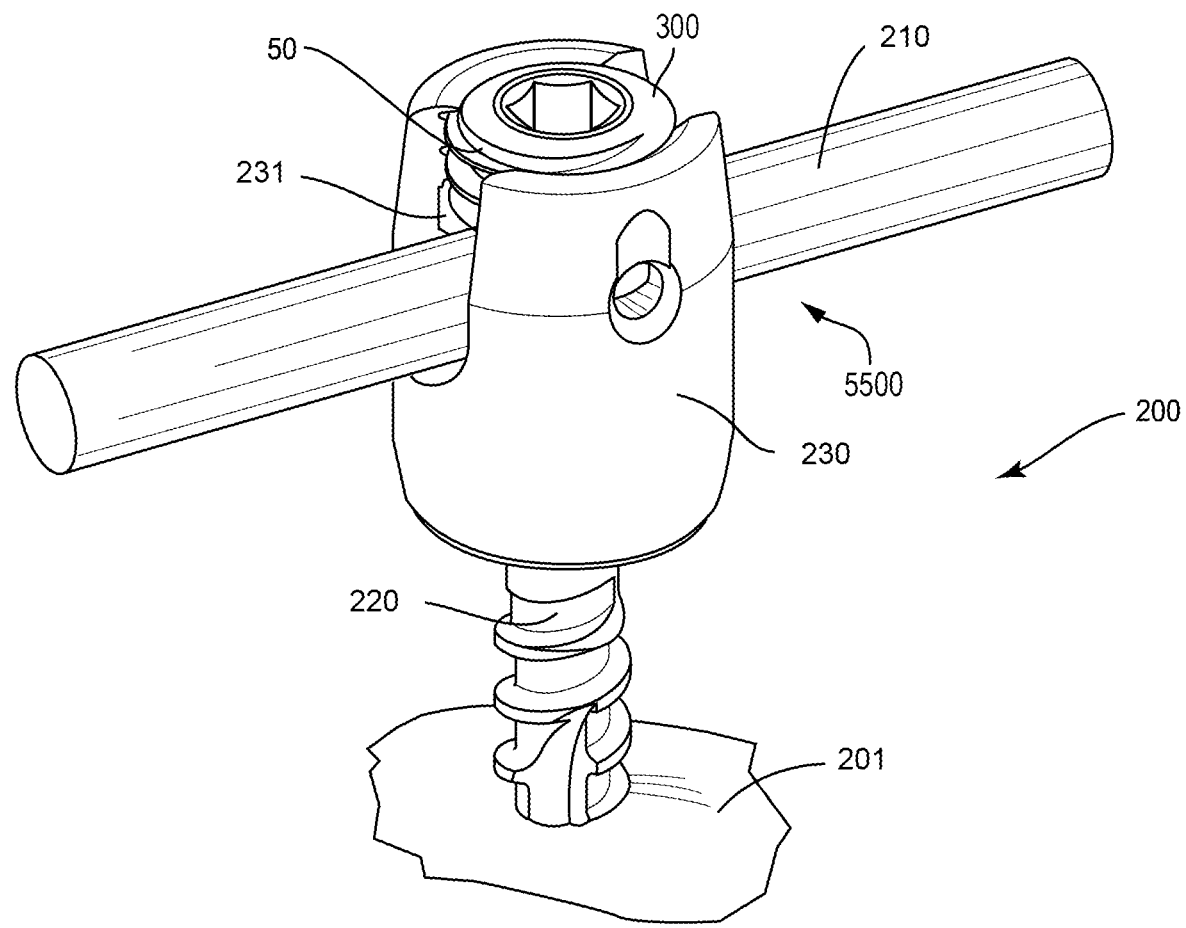
FIG. 4 is a perspective view a vertebral pedicle screw system including a digital set screw.
Figure 5:
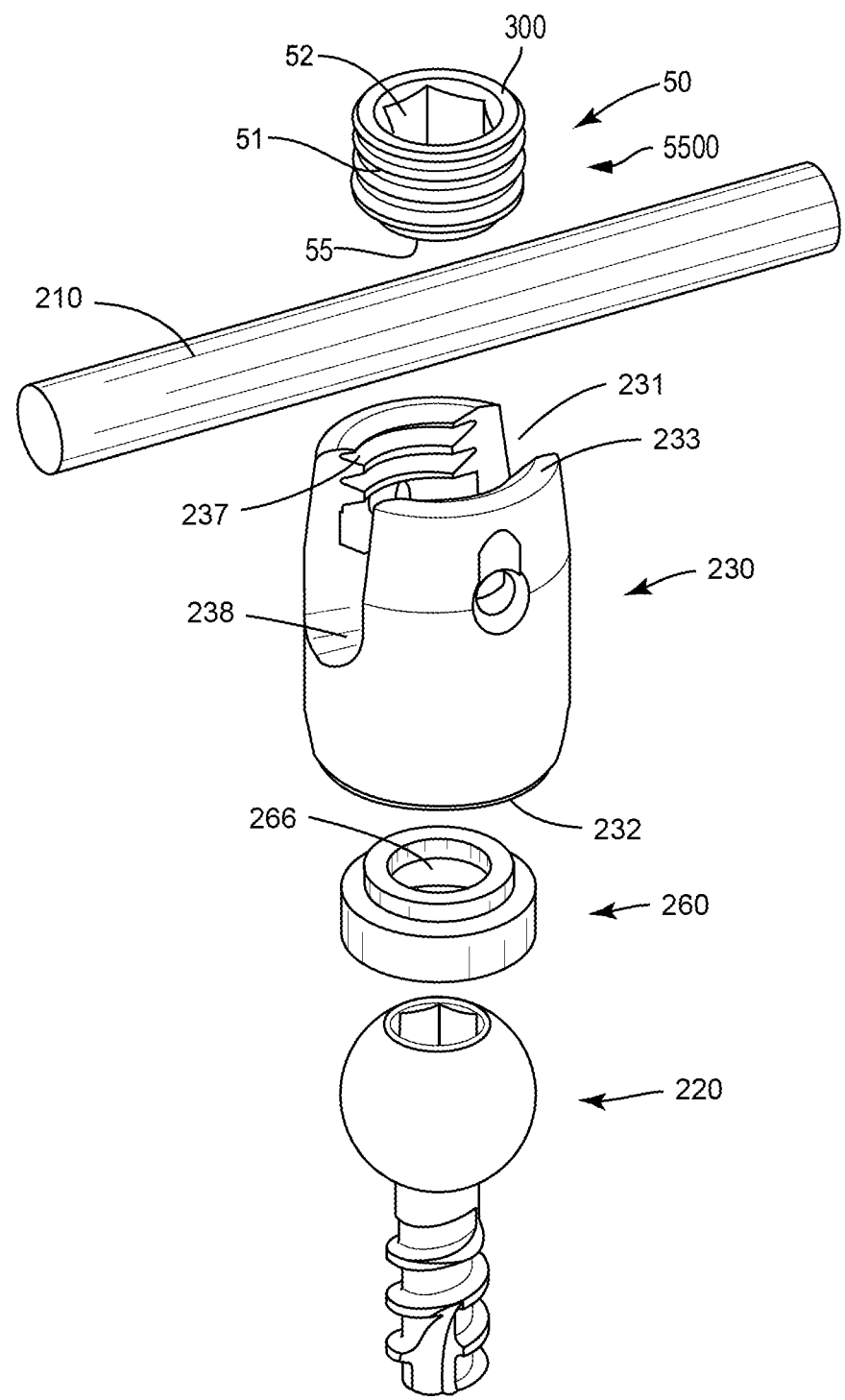
FIG. 5 is an exploded parts view of a vertebral pedicle screw system including a digital set screw.

FIG. 4 is a perspective view of a vertebral pedicle screw system 200 including a digital set screw 50 and FIG. 5 is an exploded parts view of a vertebral pedicle screw system 200 including a digital set screw. FIGS. 4-5 illustrate an example medical implant system, in the form of a vertebral pedicle screw system 200 and related components and a a digital set screw 50 in accordance with the principles of the present disclosure. However, the application of probe reader 100 is not limited to the specific embodiments of vertebral pedicle screw system 200.

The components of the vertebral pedicle screw system 200 described herein can be fabricated from biologically acceptable materials suitable for medical applications, including metals, synthetic polymers, ceramics and bone material and/or their composites. For example, the components of the vertebral pedicle screw system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the vertebral pedicle screw system 200 may be formed or constructed material composites, including the above materials, to achieve various desired characteristics such as strength, rigidity, elasticity, compliance, biomechanical performance, durability and radiolucency or imaging preference. The components of the present vertebral pedicle screw system, individually or collectively, may also be fabricated from a heterogeneous material such as a combination of two or more of the above-described materials. The components of the vertebral pedicle screw system may be monolithically formed, integrally connected or include fastening elements and/or instruments, as described herein. The components of the vertebral pedicle screw system may be formed using a variety of subtractive and additive manufacturing techniques, including, but not limited to machining, milling, extruding, molding, 3D-printing, sintering, coating, vapor deposition, and laser/beam melting. Furthermore, various components of the vertebral pedicle screw system may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

The vertebral pedicle screw system 200 may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the vertebral pedicle screw system may be employed with surgical procedures, as described herein, and/or, for example, corpectomy, discectomy, fusion and/or fixation treatments that employ spinal implants to restore the mechanical support function of vertebrae. In some embodiments, the pedicle screw system may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), transforaminal lumbar Interbody fusion (TLIF), posterior lumbar Interbody fusion (PLIF), various types of posterior or anterior fusion procedures, and any fusion procedure in any portion of the spinal column (sacral, lumbar, thoracic, and cervical, for example).

FIG. 5 may illustrate an example anchoring assembly and longitudinal member 210 according to an embodiment. As illustrated in FIG. 5, an anchoring assembly may include a screw 220 and an anchoring member 230. The screw 220 may have an elongated shape with a first end mounted within a vertebral member 201 and a second end extending outward above the vertebral member 201. The anchoring member 230 may be configured to operatively connect to the second end of the screw 220 and may be movably connected to the screw 220 to accommodate the longitudinal member 210 positioned at various angular positions. The anchoring member 230 may include a channel 231 sized to receive the longitudinal member 210. A set screw 50 may attach to the anchoring member 230 to capture the longitudinal member 210 within the channel 231.

FIG. 5 illustrates an example exploded view of a screw assembly and longitudinal member 210 according to an embodiment. As shown by FIG. 5, anchoring member 230 provides a connection between the screw 220 and longitudinal member 210. Anchoring member 230 includes a first end 232 that faces towards the vertebral member 201, and a second end 233 that faces away. A chamber may be positioned between the first and second ends 232, 233 and may be sized to receive at least a portion of the screw 220. In various embodiments, a first end 232 may be considered a base portion of an anchoring member 230, and a second end 233 may be considered a head portion of an anchoring member.

The second end 233 of the anchoring member 230 may include a channel 231 sized to receive the longitudinal member 210. Channel 231 terminates at a lower edge 238 that may include a curved shape to approximate the longitudinal member 210. Threads 237 may be positioned towards the second end 233 to engage with the set screw 50. In one embodiment as illustrated in FIG. 5, the threads 237 are positioned on the interior of the anchoring member 230 facing towards the channel 231. In another embodiment, the threads 237 may be on the exterior of the anchoring member 230. An interior of the anchoring member 230 may be open between the first and second ends 232, 233.

In various embodiments, an anchoring member 230 may include a washer 60. A washer 60 may be generally cylindrical and may have a hole 66 there through. As illustrated by FIG. 5 a washer 60 may be positioned near a first end 232 of an anchoring member 230. A screw 220 may engage with an anchoring member 230 via positioning through the hole 66 of a washer 60. A washer 60 may include recessed portions which may be configured to accommodate placement of a longitudinal member 210 therein. The use of a washer 60 in connection with an anchoring member 230 may help minimize misalignment of the longitudinal member within the anchoring member.

In an embodiment, set screw 50 attaches to the anchoring member 230 and captures the longitudinal member 210 within the channel 231. Set screw 50 may include an antenna 300, which will be explained in further detail below. As illustrated in FIG. 5, the set screw 50 may be sized to fit within the interior of the channel 231 and include exterior threads 51 that engage threads 237 on the anchoring member 230. Additionally, a cover portion 55 may contact longitudinal member 210 when the set screw 50 is rotatably positioned into a closed contact position above longitudinal member 210 and within anchoring member 230. A driving feature 52 may be positioned on a top side to receive a tool during engagement with the anchoring member 230, e.g., a screwdriver or the like having a corresponding head. In some embodiments, the set screw 50 may be mounted on an exterior of the anchoring member 230. Set screw 50 may include a central opening that partially extends into set screw 50 from drive feature 52 towards the second end 233. For example, the drive feature 52 may be a recessed portion having a covered bottom portion and circumferential side walls such that the drive feature 52 portion of set screw 50 does not fully extend through the set screw 50 from the top to the bottom. Threads 51 are positioned on an outside surface of the set screw 50 and engage with the threads 237 on the anchoring member 230. The set screw 50 and anchoring member 230 may be constructed for the top side of the set screw 50 to be flush with or recessed within the second end 233 when mounted with the anchoring member 230. For example, a common plane crossing over a top surface of antenna 300 and a top surface of second end 233.

Although FIGS. 4 and 5 illustrate an exemplary multi-axial tulip-head pedicle screw it shall be understood that other types of anchoring members may be used within the scope of this disclosure. For example, fixed head screws or screws having differently shaped heads may be used. As another example, a hook member, a cross-link connector, an offset connector, or a hybrid hook-screw member may be used as well.

Figure 6:
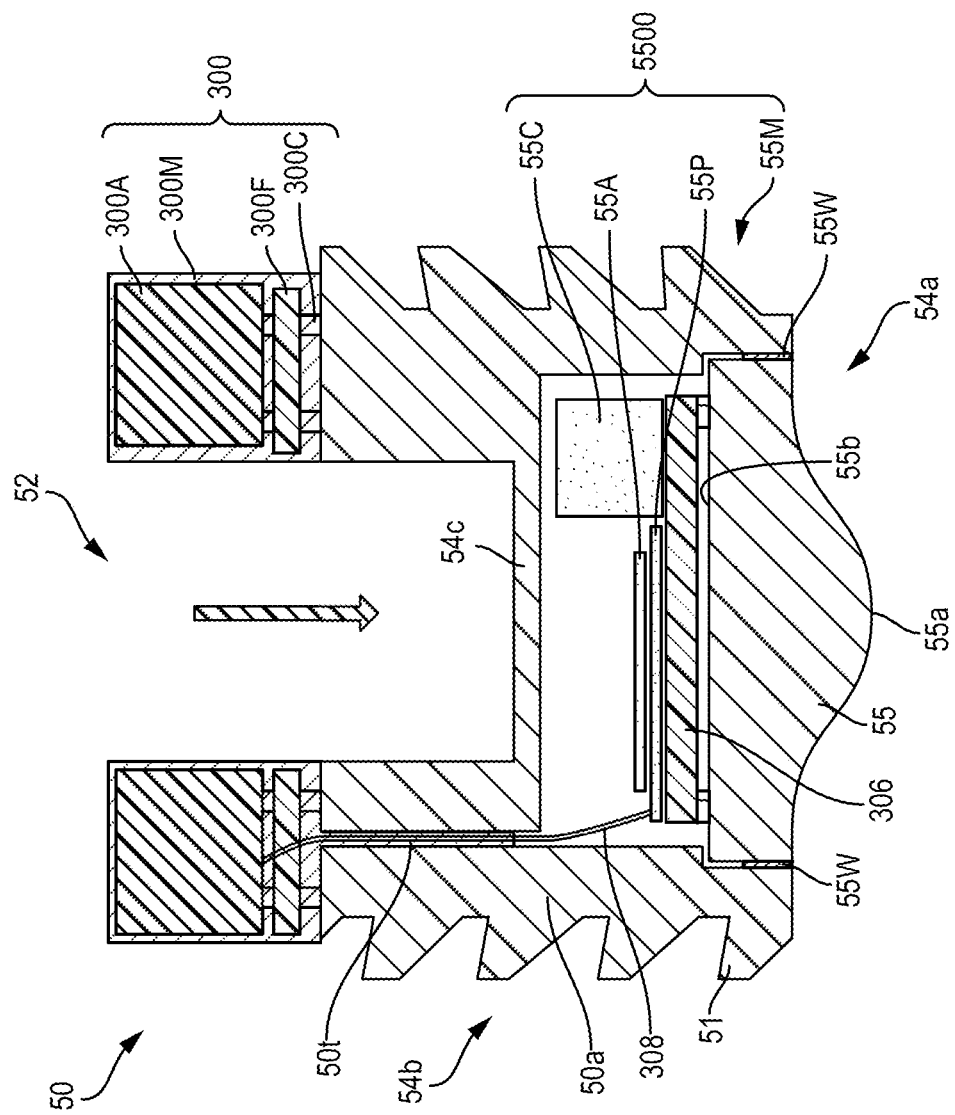
FIG. 6 is a cross section view of a digital set screw.

FIG. 6 is a cross section view of a digital set screw 50. FIG. 6 illustrates a cross section drawing of an example set screw 50 of FIGS. 4-5. In the example illustration, antenna 300 may be disposed on a top portion of main body 50a and cover portion 55 may be disposed in a lower cover cavity 54a of main body 50a. In example embodiments, antenna 300, may be a radio frequency identification (RFID) coil, a near field-communication (NFC) antenna or other short-range communication transmitter and/or receiver. Antenna 300 may include an axisymmetric coil 300a stacked on a ferrite base 300f and a carrier 300c. The axisymmetric coil 300a, ferrite 300f, and carrier 300c may be surrounded by an overmold 300m. An example overmold 300m may be an insulator material, such as a thermoplastic material like Polyether ether ketone (PEEK). In some embodiments, antenna 300 may be fixedly coupled to a top portion of set screw 50 and in other embodiments, antenna 300 may be removably coupled to a top portion of set screw 50, e.g., by mechanical means such as corresponding threads or snap locking features.

In an example embodiment, set screw 50 may include a drive feature 52 that passes through antenna 300 and into a cavity of set screw 50 that is defined by interior sidewalls of set screw 50 and a bottom sidewall 54c. Antenna 300 may also include a flexible electronics component, such as, for example, a flex circuit or one or more electrical circuits operably connected to the electronics components 5500 via a connecting member 308. For instance, as shown in FIG. 6, the connecting member 308 may be connected to both the antenna 300 and the electronics components 5500. The connecting member 308 may be positioned perpendicularly to both the antenna 300 and the electronics components 5500. In an example embodiment, connecting member 308 may pass from antenna 300 through a through hole 50*t* passing through main body 50*a* and into electronics cavity 54*b* for housing electronics components 5500. In an example embodiment, through hole 50*t* may be filled with an insulating material, for example the same or substantially same material as the overmold 300*m*. However, it shall be understood that through hole 50*t* may be filed with any suitable material that is effective at sealing through hole 50*t*, e.g., an epoxy or the like.

Example, electronics components 5500 may include a series of electronic components in electrical communication with one another. For example, a mainboard or other suitable printed circuit board (PCB) 55*p* may be electrically connected to an application specific integrated circuit (ASIC) 55*a*, a charge storage capacitor 55*c,* and various mechanical electrical sensors (MEMs) 55*m*. Example MEMs 55*m* may include a strain gauge, and/or a temperature gauge. However, other MEMs sensors may be incorporated in other embodiments depending on the particular use case. In some embodiments, electronics components 5500 may be an pre-packaged self-contained unit that is attached to cover 55 by, e.g., adhesive, chemical, mechanical or cement bonding. Additionally, electronics components 5500 may include a non-transitory data store (not illustrated) according to an embodiment, e.g., a memory cell such as a solid state memory cell or the like. The non-transitory memory data store may store information and/or data from various MEMs sensors 55*m,* for example. A non-transitory data store may be used to store various information. For example, one or more measurements of a strain gauge 306 may be stored in memory. As another example, a unique identifier associated with a load sensing assembly, a component thereof, or a set screw 50 may be stored in memory. Additional and/or alternate information or types of information may be stored as is consistent with this disclosure. Additionally, in some embodiments, electronics components 5500 may be coated in a material to prevent and/or suppress corrosion, e.g., a conformal coating, an epoxy coating, aerosol coating, or the like.

In various embodiments, electronics components 5500 may be fixedly coupled to cover portion 55 and have a connecting terminal or connecting portion 308 extending therefrom. The connecting terminal or connecting portion 308 may be suitably connected to a lead wire extending from antenna 300. For example, as shown in FIG. 6, electronics components 5500 are in electrical communication with antenna 300 by way of connecting portion 308. In various embodiments, connecting member 308, antenna 300, and/or electronics components 5500 may be constructed integrally or may be separately constructed and attached together in any suitable manner, such as for example by adhesive, chemical, mechanical or cement bonding.

In at least one embodiment, electronics components 5500 may be configured as a load sensing assembly. A load sensing assembly may include one or more electronics components 304 and/or a strain gauge 306, such as for example a silicon strain gauge. A strain gauge 306 may be a device that measures strain on an object. For instance, a strain gauge 306 may measure a force between a set screw and a longitudinal member when the set screw is engaged with an anchoring member. A strain gauge 306 may include one or more sensors or sensor nodes that measure strain, force, resistance, deflection, load and/or the like.

Figure 7:
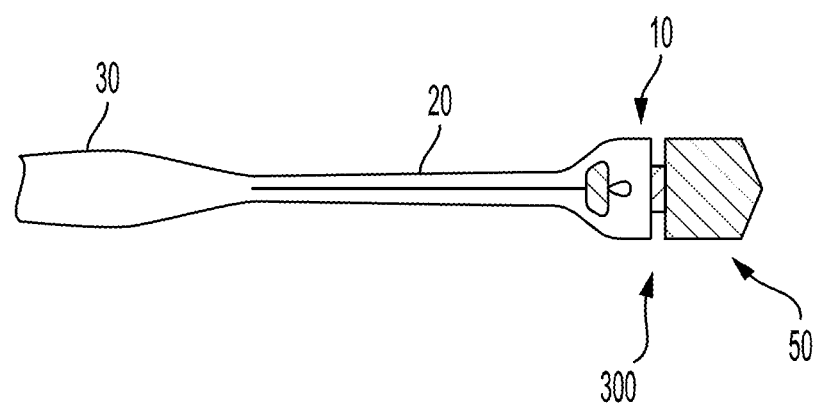
FIG. 7 is a cross section view of a surgical probe reader having a faraday cage surrounding an antenna portion of a digital set screw.

FIG. 7 is a cross section view of a surgical probe reader 100 having a faraday cage 10 surrounding an antenna portion 300 of a digital set screw 50. In the example embodiment, the faraday cage 10 may have a size and shape generally corresponding to a size and shape of antenna portion 300. For example, faraday cage 10 may have a generally circular shape defined by a first radius and set screw 50 may have a generally circular shape defined by a second radius, for example. Additionally, the first radius may approximate the size of the second radius and/or be the same size as the second radius, for example. In at least some embodiments, the first radius may be greater than the second radius such that the faraday cage 10 surrounds the outer perimeter of set screw 50. In other embodiments, the faraday cage 10 may rest on top of digital set screw 50 and have a radius that is less than the radius of digital set screw 50. In either case, the faraday cage 10 may allow for the transmission of electromagnetic signals from digital set screw 50 while blocking out electromagnetic signals from other electronic devices, including but not limited to other digital set screws.

Figure 8:
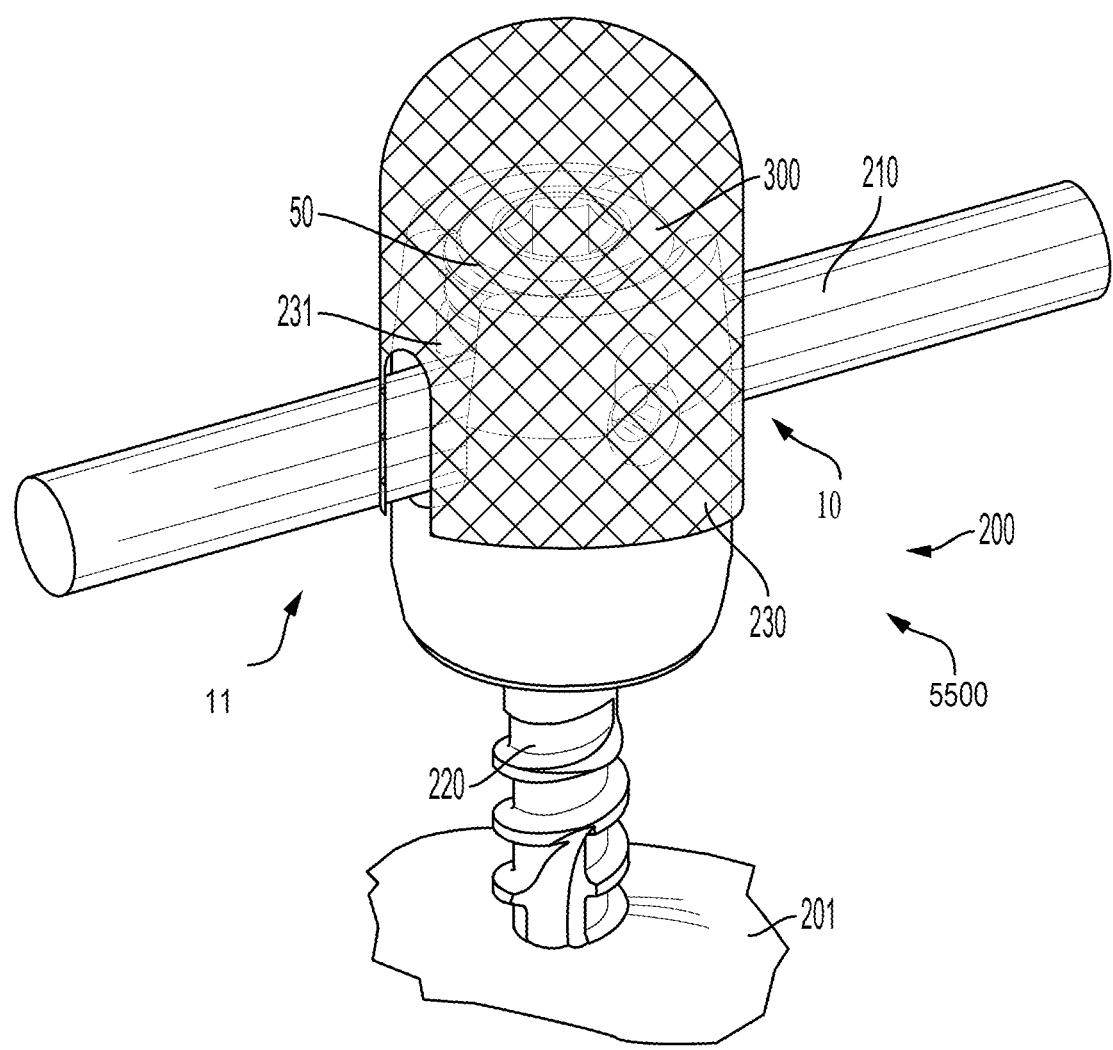
FIG. 8 is an image of a faraday cage surrounding an antenna of digital set screw of a pedicle screw system.

FIG. 8 is an image of a faraday cage 10 in skeleton lines surrounding an antenna portion of a digital set screw 50. In various embodiments, the faraday cage 10 may have a hollow receiving cavity at a distal end thereof that may be slipped over a spinal construct, for example a vertical pedicle screw system of FIG. 4 and those above explained components. In the example embodiment of FIG. 8, the faraday cage 10 may include a circular shaped distal end and/or a circular shaped receiving cavity having a first and second slots 11 (may also be referred to as cutouts). In various embodiments, the first and second slot may have a size and shape generally corresponding to a cross-sectional diameter of rod 210. For example, the faraday cage 10 may be positioned such that it surrounds the digital set screw 50 (at least in the lateral direction) and the longitudinal rod is positioned within the first and second slots 11. Accordingly, the faraday cage 10 may block interference and/or cross talk with other electronics components and/or other digital set screws 50.

Figure 9:
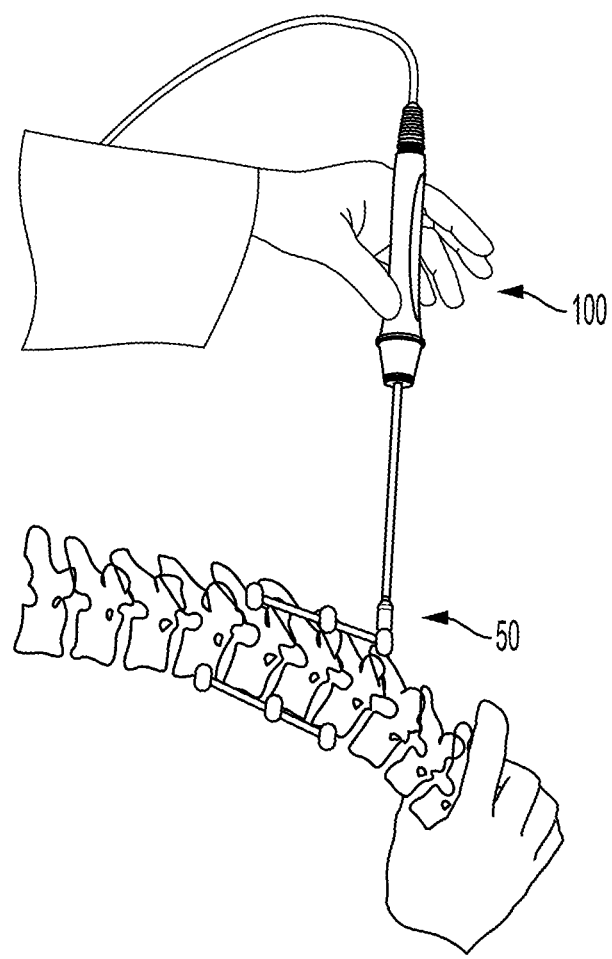
FIG. 9 is an image of a surgical probe reader being used to assign location information to a first digital set screw of a plurality of digital set screws.

FIG. 9 is an image of a surgical probe reader 100 being used to assign location information to a first digital set screw 50 of a plurality of digital set screws 50. In the example embodiment, it is illustrated where a spinal implant system includes a plurality of vertebral pedicle screws 220 and corresponding anchoring members 230 that are coupled together via a longitudinal rod 210, for example. As explained above, the longitudinal rod 210 may be secured within each of the plurality of anchoring members 230 by a plurality of corresponding digital set screws 50. Applicants have discovered a particular problem where the various set screws 50 may create cross talk and/or interference making it difficult for an end user such as a surgeon to assign identity information such as location information to each of the respective set screws 50. Accordingly, embodiments in accordance with the principles of this disclosure provide for a probe reader 100 having a faraday cage 10. In practice, and as illustrated by FIG. 9, the end user may place the faraday cage 10 around any one of the various set screws 50 to assign identity information, receive pre-assigned identity information, and or read other information from the digital set screw 50, for example. An example method of operation is disclosed below in conjunction with FIG. 10.

Figure 10:
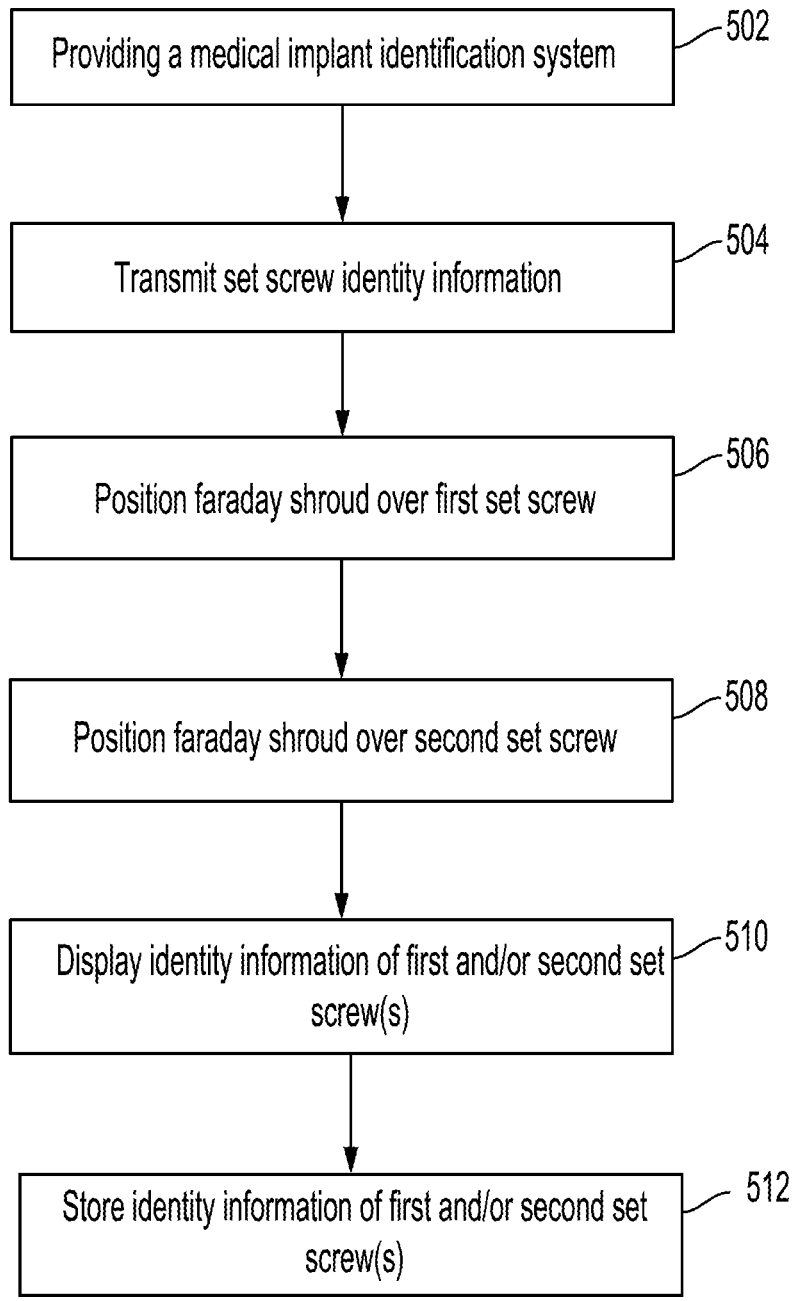
FIG. 10 is an example method of operation of a surgical probe reader.

FIG. 10 is an example flow chart concerning a method of operation 500 of using a surgical probe reader 100 to independently acquire identity information of a plurality of set screws 50. The following discussion of method 500 may include reference to components, features, and functionality of probe reader 100 and implant system 200 as explained above for context, however, the method as disclosed below is not limited to the specific probe reader 100 and implant system 200 embodiments disclosed above. At step 502, a medical implant identification system may be provided. For example, a probe reader 100, an operating room console 65 including a display, and a plurality of set screws 50 associated with a medical construct such as the vertebral pedicle screw system 200 disclosed above. At step 504, each of the various set screws 50 may independently transmit set screw specific identity information, for example. For example, a first antenna of a first set screw may transmit first identity information associated with the first set screw and a second antenna of a second set screw may transmit second identity information associated with the second set screw, for example. In various embodiments, the identity information of the first and second set screws may be transmit simultaneously or in sequence. At step 506, the faraday cage 10 of the probe reader 100 may be positioned over the antenna of the first set screw 50, for example. Concurrently, the probe reader 100 may receive the first identity information of the first set screw while also blocking interference associated with the second identity information of the second set screw due to the faraday cage, for example. At step 508, the faraday cage 10 of the probe reader 100 may be positioned over the antenna of the second set screw 50, for example. Concurrently, the probe reader 100 may receive the second identity information of the second set screw 50 while also blocking interference associated with the first identity information of the first set screw due to the faraday cage, for example. At step 510, identity information of the first set screw may be displayed by the display 67 and/or identity information of the second set screw may be displayed by the display 67, for example. At step 512, identity information previously received by the probe reader 100 may be stored in a computer readable non-transitory medium, such as a data store or the like associated with the operating console 65 and/or display 67. In various embodiments, a data store may comprise conventional memory of a computer, such as a hard drive (which may be a solid state drive, DRAM, NAND flash memory, etc.). Connections and interactions between the units described herein may be hardwired, wireless, cloud-based, and/or in the form of local physically stored data (e.g., as data stored in and retrieved from memory of a computer, such as a register, buffer, cache, storage drive, etc., such as part of an application programming interface (API)), for example. In various embodiments, a data store may comprise conventional memory of a computer, such as a hard drive (which may be a solid state drive, DRAM, NAND flash memory, etc.).

As explained herein, various embodiments of a surgical probe reader 100 for use with various digital set screws 50 is described in detail. Additionally, various methods of operation of using a surgical probe reader 100 having a faraday cage to accurately read identity information of a single set screw of a plurality of set screws is described. For example, in summary a probe reader 100 having a faraday cage 10 may read identity information of a first set screw 50 of a plurality of set screws 50 while eliminating, suppressing, and/or isolating interference associated with the remaining set screws 50 of the plurality of set screws 50.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A medical implant identification system, comprising:
   a probe reader extending from a proximal end to a distal end in a proximal-to-distal direction, the distal end including a faraday cage;
   a display in communication with the probe reader;
   an operating console in communication with the probe reader and the display, and
   a set screw comprising an antenna disposed in an antenna portion of the set screw and at least one sensor in communication with the antenna,
   wherein:
   the faraday cage has a size and shape corresponding to a size and shape of the antenna portion,
   the antenna is configured to transmit identity information of the set screw to the probe reader,
   the antenna is configured to transmit sensor information received from the at least one sensor to an external device, and
   the operating console is configured to store identity information of the set screw in a non-transitory computer readable data storage medium.

2. The medical implant identification system of claim 1, wherein the antenna portion is disposed proximate a top portion of the set screw.

3. The medical implant identification system of claim 2, wherein, in a reading position, the faraday cage of the probe reader surrounds the antenna portion.

4. The medical implant identification system of claim 3, wherein:
   the antenna portion further comprises a circular overmold defined by a first diameter,
   the faraday cage comprises a circular shape defined by a second diameter, and
   the first diameter approximates the second diameter, and the second diameter is larger than the first diameter.

5. The load sensing assembly of claim 1, wherein the display is configured to show identity information of the set screw.

6. The load sensing assembly of claim 5, wherein the at least one sensor comprises one or more of the following: a strain gauge, impedance sensor, pressure sensor, and capacitive sensor.

7. The load sensing assembly of claim 1, wherein, in a reading position, the faraday cage of the probe reader surrounds the antenna portion.

8. The load sensing assembly of claim 1, wherein the at least one sensor is configured to sense an external force applied to the set screw.

9. The load sensing assembly of claim 1, wherein the antenna is powered by electromagnetic energy.

10. The load sensing assembly of claim 1, wherein:
the probe reader further comprises a first coil and a second coil disposed proximate the distal end, and
the faraday cage covers the first coil and second coil.

11. The load sensing assembly of claim 10, wherein the first coil extends in the proximal-to-distal direction and the second coil extends in a lateral direction that is substantially perpendicular to the proximal-to-distal direction.

12. The load sensing assembly of claim 1, wherein the probe reader is powered by the operating console.

13. The load sensing assembly of claim 1, wherein the probe reader is in communication with the display via a wired cable.

14. A medical implant identification system, comprising:
a probe reader extending from a proximal end to a distal end in a proximal-to-distal direction, the distal end including a faraday cage;
a display in communication with the probe reader;
a first set screw comprising an antenna disposed in a first antenna portion of the first set screw and at least one first sensor in communication with the first antenna; and
a second set screw comprising a second antenna disposed in a second antenna portion of the second set screw and at least one second sensor in communication with the second antenna,
wherein:
the faraday cage has a size and shape corresponding to a size and shape of the first antenna portion and the second antenna portion,
the first antenna is configured to transmit first identity information to the probe reader, and is configured to transmit first sensor information received from the at least one sensor to an external device, and
the second antenna is configured to transmit second identity information to the probe reader, and is configured to transmit second sensor information received from the at least one second sensor to an external device.

15. The medical implant identification system of claim 14, wherein:
in a first reading position, the faraday cage of the probe reader surrounds the first antenna portion thereby receiving the first identity information of the first set screw and blocking interference associated with the second identity information of the second set screw, and
in a second reading position, the faraday cage of the probe reader surrounds the second antenna portion thereby receiving the second identity information of the second set screw and blocking interference associated with the first identity information of the first set screw.

16. The medical implant identification system of claim 14, further comprising an operating console in communication with the probe reader and the display, the operating console being configured to store the first identity information of the first set screw and the second identity information of the second set screw in a non-transitory computer readable data storage medium.

17. A method for isolating identity information of a set screw, comprising:
providing a medical implant identification system, the medical implant identification system comprising:
a probe reader extending from a proximal end to a distal end in a proximal-to-distal direction, the distal end including a faraday cage;
a display in communication with the probe reader;
an operating console in communication with the probe reader;
a first set screw comprising an antenna disposed in a first antenna portion of the first set screw and at least one first sensor in communication with the first antenna; and
a second set screw comprising a second antenna disposed in a second antenna portion of the second set screw and at least one second sensor in communication with the second antenna,
wherein:
the faraday cage has a size and shape corresponding to a size and shape of the first antenna portion and the second antenna portion,
the first antenna is configured to transmit first identity information to the probe reader, and is configured to transmit first sensor information received from the at least one sensor to an external device,
the second antenna is configured to transmit second identity information to the probe reader, and is configured to transmit second sensor information received from the at least one second sensor to an external device,
positioning the faraday cage of the probe reader around the first antenna portion; receiving the first identity information of the first set screw; and
blocking interference associated with the second identity information of the second set screw.

18. The method for isolating identity information of claim 17, comprising:
positioning the faraday cage of the probe reader around the second antenna portion;
receiving the second identity information of the second set screw; and
blocking interference associated with the first identity information of the first set screw.

19. The method for isolating identity information of claim 18, comprising:
displaying identity information of the first set screw on the display; and
displaying identity information of the second set screw on the display.

20. The method for isolating identity information of claim 18, comprising:
storing identity information of the first set screw in a non-transitory data storage medium associated with the operating console; and
storing identity information of the second set screw in a non-transitory data storage medium associated with the operating console.

* * * * *